United States Patent
Ester

(10) Patent No.: US 9,506,844 B2
(45) Date of Patent: Nov. 29, 2016

(54) MEASURING DEVICE FOR MEASURING DUST IN FLUE GAS

(71) Applicant: Stephan Ester, Bad Wuennenberg (DE)

(72) Inventor: Stephan Ester, Bad Wuennenberg (DE)

(73) Assignee: Woehler Technik GmbH, Bad Wuennenberg (DE)

(*) Notice: Subject to any disclaimer, the term of this patent is extended or adjusted under 35 U.S.C. 154(b) by 172 days.

(21) Appl. No.: 14/388,591

(22) PCT Filed: Mar. 25, 2013

(86) PCT No.: PCT/DE2013/000163
§ 371 (c)(1),
(2) Date: Sep. 26, 2014

(87) PCT Pub. No.: WO2013/143523
PCT Pub. Date: Oct. 3, 2013

(65) Prior Publication Data
US 2015/0059443 A1   Mar. 5, 2015

(30) Foreign Application Priority Data
Mar. 27, 2012 (DE) .................. 10 2012 006 052

(51) Int. Cl.
*G01N 1/22* (2006.01)
*G01N 33/00* (2006.01)
*G01N 5/00* (2006.01)
G01N 15/06 (2006.01)
G01N 15/00 (2006.01)

(52) U.S. Cl.
CPC .............. *G01N 1/2258* (2013.01); *G01N 5/00* (2013.01); *G01N 33/0009* (2013.01); *G01N 15/0618* (2013.01); *G01N 2001/2261* (2013.01); *G01N 2001/2285* (2013.01); *G01N 2015/0096* (2013.01); *G01N 2291/02408* (2013.01)

(58) Field of Classification Search
CPC ................ G01N 2291/02408; G01N 33/009; G01N 2001/2261; G01N 2001/2285; G01N 1/2258; G01N 2201/0225; G01N 2201/024; G01N 2201/0245; G01N 2035/00306; G01N 2035/00326; G01D 11/30
See application file for complete search history.

(56) References Cited

U.S. PATENT DOCUMENTS

| | | | |
|---|---|---|---|
| 3,926,271 A | 12/1975 | Patashnick | |
| 4,154,088 A | 5/1979 | Werner | |
| 4,442,699 A * | 4/1984 | Ramelot | ............. G01N 1/2247 73/28.01 |
| 5,694,208 A | 12/1997 | Ichikawa | |
| 6,016,688 A | 1/2000 | Hiss, III et al. | |
| 6,192,767 B1 | 2/2001 | Fiorina | |
| 6,422,060 B1 * | 7/2002 | Patashnick | ............. G01N 15/02 73/28.01 |
| 7,111,496 B1 | 9/2006 | Lilienfeld et al. | |
| 7,292,338 B2 | 11/2007 | Itagaki | |
| 7,947,503 B2 * | 5/2011 | Tuchman | ............. G01N 1/2205 177/210 FP |

FOREIGN PATENT DOCUMENTS

| | | |
|---|---|---|
| CN | 202075193 | 12/2011 |
| DE | 25 53 638 | 8/1976 |
| DE | 197 27 969 | 1/1999 |

(Continued)

*Primary Examiner* — Justin Olamit
(74) *Attorney, Agent, or Firm* — Cozen O'Connor

(57) ABSTRACT

A measuring device for measuring dust in flue gas of small-scale furnace installations for solid fuels includes: a measuring probe; a weighing device having a filter device; a heated suction hose connecting the measuring probe to the weighing device; and a weighing module in which the weighing device is arranged. The weighing device is thermally insulated in the weighing module.

9 Claims, 2 Drawing Sheets

(56) References Cited

FOREIGN PATENT DOCUMENTS

| DE | 696 27 922 T2 | 3/2004 |
| DE | 10 2005 009 582 A1 | 8/2006 |
| DE | 10 2006 039 670 A1 | 3/2007 |
| DE | 10 2006 026002 A1 | 12/2007 |
| DE | 10 2007 041 369 A1 | 2/2009 |
| WO | WO 99/41601 | 8/1999 |
| WO | WO 2006/138375 | 12/2006 |

* cited by examiner

MEASURING DEVICE FOR MEASURING DUST IN FLUE GAS

CROSS-REFERENCE TO RELATED APPLICATIONS

This is a U.S. national stage of application No. PCT/DE2013/000163, filed on 25 Mar. 2013, which claims priority to the German Application No. 10 2012 006 052.1, filed 27 Mar. 2012, the content of both incorporated herein by reference.

BACKGROUND OF THE INVENTION

1. Field of the Invention

The invention is directed to a measuring device, particularly for measuring dust in the flue gas of small-scale furnace installations for solid fuels, having a measuring probe and a heated suction hose connecting the measuring probe to a weighing device with a filter device.

2. Related Art

In 2010, the First Ordinance Concerning the Implementation of the Federal Emissions Control Act was amended by the Ordinance Governing Small-scale and Medium-scale Furnace Installations (1st BImSchV) with the goal of substantially contributing to reducing emissions of fine particulates from small-scale furnace installations. In particular, the use of wood in furnace installations within the scope of the Ordinance Governing Small-scale and Medium-scale Furnace Installations can make an important contribution to achieving climate protection goals. However, the combustion of biomass can lead to emissions that are hazardous to health as well as fine particulate matter, for example, due to the release of various air pollutants.

To achieve climate goals, 1st BImSchV stipulates regular monitoring of furnace installations and prescribes maximum levels for fine particulate matter in the flue gas depending on the type of furnace installations.

For newer furnace installations, limiting values of 0.02 g/m$^3$ are called for as of 2015. These limiting values present a challenge to metrology even though the basic principle is simple and remains the same, namely, to guide a predefined amount of the flue gas of a furnace installation through a filter and ascertain the difference of mass before and after the measuring process in order to determine the fine particulates content in the flue gas.

In order to measure such small quantities of dust, optical systems such as those described, for example, in DE 10 2006 039670 A1, DE 10 2005 009582 A1 or DE 6 9627922 T2 are currently favored in technical development.

In optical systems for determining a quantity of dust in a flue gas, the varying constitution of the dust particles and, therefore, the reflectivity thereof, must be considered fundamentally disadvantageous so that, in particular, the measurement of very small quantities of dust by optical methods seems inherently problematic.

DE 2 553 638 C2 shows an alternative to conventional scales. A device mentioned in this reference has an elastic element in the form of a hollow pipe that narrows in diameter from a clamped-in first end toward a second, free end. The free end of the pipe is widened and carries a platform-like base for articles to be weighed. The mass of the article to be weighed can be deduced from the change in the resonant frequency of the vibratory pipe in a loaded condition and when loaded by the article to be weighed. An accurate weighing of a sample appears possible with this device, but this known device is fundamentally unsuited for analyzing flue gas in a solid fuel furnace.

In a measuring method mentioned in DE 10 2007 041 369 A1 in order to determine the amount of dust in the flue gas of a solid fuel furnace, a predefined amount of the flue gas flews through a vibratory tube, whereupon a quantity of dust deposits on a filter device of the tube. The tube is set in oscillation and the dust quantity is calculated from the deviation from the predetermined resonant frequency and/or natural frequency of the tube by an evaluating device.

Apart from the weighing device, the hose connections between a measuring probe to be introduced into the flue gas flow and the actual measuring device are of considerable importance. A measuring device with a weighing device comparable to DE 2 553 638 C2 is known from U.S. Pat. No. 7,947,503 B2. In this measuring device, a heated suction hose is provided between a gas inlet opening and the weighing device. By heating the suction hose, particles are prevented from depositing in the hose upstream of the weighing device and distorting the measurement results. Measuring accuracy is appreciably increased through this step.

However, the measuring device known from U.S. Pat. No. 7,947,503 B2 is not suitable for measuring fine particulates compliant to 1st BImSchV.

SUMMARY OF THE INVENTION

Against this technical background, an object of the invention is to provide a practice-oriented measuring device in which, in particular, the fine particulates measurements according to 1st BImSchV can be carried out in a simple manner but very accurately.

In one aspect of the present invention, in a measuring device, particularly for measuring dust in the flue gas of small-scale furnace installations for solid fuels, having a measuring probe and a heated suction hose connecting the measuring probe to a weighing device with a filter device as set forth herein, the above-stated set of technical problems is remedied through the features consisting in that the weighing device is arranged in a weighing module, and in that the weighing device is thermally insulated in the weighing module.

The measuring device according to the invention has many advantages.

The heated hose and the thermal insulation of the weighing device ensure that, after a heating-up phase, there is hardly any condensation or the like precipitation on the path from the probe to the location where the fine particulate matter is separated and weighed.

In this way in particular, precipitators of any kind upstream of the weighing location can be dispensed with, as can the admixture of fresh air.

To avoid this heating-up phase by a flue gas, it is further provided in a preferred embodiment of the measuring device according to the invention that the weighing device is arranged in a heatable sleeve in the weighing module.

While the suction hose is continuously held at a reference temperature of about 75° C. by the heating during a measurement, only a pulsed heating with a duration of about one minute is required prior to measurement with the sleeve enclosing the weighing device. When the temperatures in the suction hose and weighing device have stabilized, the actual measurement can take place, and it is then also ensured that there will be no significant precipitation in the suction hose or weighing device.

In addition to user friendliness of the measuring device, the invention also provides for an exact measurement of a flue gas particularly of a small-scale furnace installation for solid fuels. These measurements are to be carried out at a flue gas temperature of about 70°. In order for the suction hose to be conditioned in a corresponding manner as well, it has proven advisable that the heating of the suction hose be carried out in a controlled manner. A hose temperature sensor arranged between the weighing device and hose is provided as an actual-temperature transducer. In particular, the hose temperature sensor is detachably connected to the weighing device and to one end of the suction hose to prevent the sensor from damage when the suction hose is bent and from falling out or the like on the one hand and to allow easy cleaning of the hose temperature sensor and flue gas hose on the other hand.

The weighing device itself has a vibratory tube arranged in the sleeve, the free end of the vibratory tube being disposed on the gas outlet side and closed by a filter cartridge fitted thereto. Preferably, the quantity of dust is determined in a manner comparable to the method known from DE 10 2007 041 369 A1, and the attached filter cartridge ensures a rapid exchange thereof, because an unused filter cartridge is required for every measurement.

User friendliness is ensured in that the weighing module is designed in a self-contained manner and can be removed from a case together with a display-and-control module on a telescoping stand.

Since the equipment required for carrying out the measurements in compliance with 1st BImSchV is extensive, and the weight, for example, of the pumps to be provided for this purpose is considerable, it is advantageous that the measuring device, including equipment, be accommodated completely within a case, for example, in an aluminum case of sufficient stability. This case can advisably be provided additionally with rollers or the like on the underside.

To carry out measurements, the weighing module, with the weighing device combined with the display-and-control module, is pulled out on a telescoping stand after opening the case until the display-and-control module is at a convenient working height for the operator. The suction hose connecting the weighing module with weighing device to the measuring probe is accordingly also pulled out of the case at the same time. When pulled out of the case in this way, the measuring probe is also easily accessible and can also be exchanged if need be.

In one aspect, it is preferable that a holding device for the heated suction hose is provided inside the case.

In one aspect, it is preferable that the weighing module with the display-and-control module is removably connected to the stand and, for example, depending on construction, is used on a further stand separate from the case. To this end, as well as for facilitating pulling out, the weighing module is provided with a handle. Also provided at the handle is an operating layer, for example, for a clamping device or the like, for unlocking from a stand.

A connection hose leads from the weighing module into the interior of the case to the pump arranged therein. Preferably, a flue gas condenser is provided, in order to protect this pump and the sensors further arranged therein. In the measuring device according to the invention, a folding case cover is preferably provided with a flue gas condenser of this type. In an open position of the cover locked vertically upward, gravitational force can be incorporated in a condensation process. The flue gas condenser is preferably fastened to the case cover so as to be detachable for cleaning, exchanging filters or the like.

In addition, a front flap further improves the accessibility of the interior of the case.

BRIEF DESCRIPTION OF THE DRAWING

The measuring device according to the invention will be described more fully with reference to the drawings which schematically show only one exemplary embodiment. In the drawings.

DETAILED DESCRIPTION OF THE PRESENTLY PREFERRED EMBODIMENTS

Figure 1:
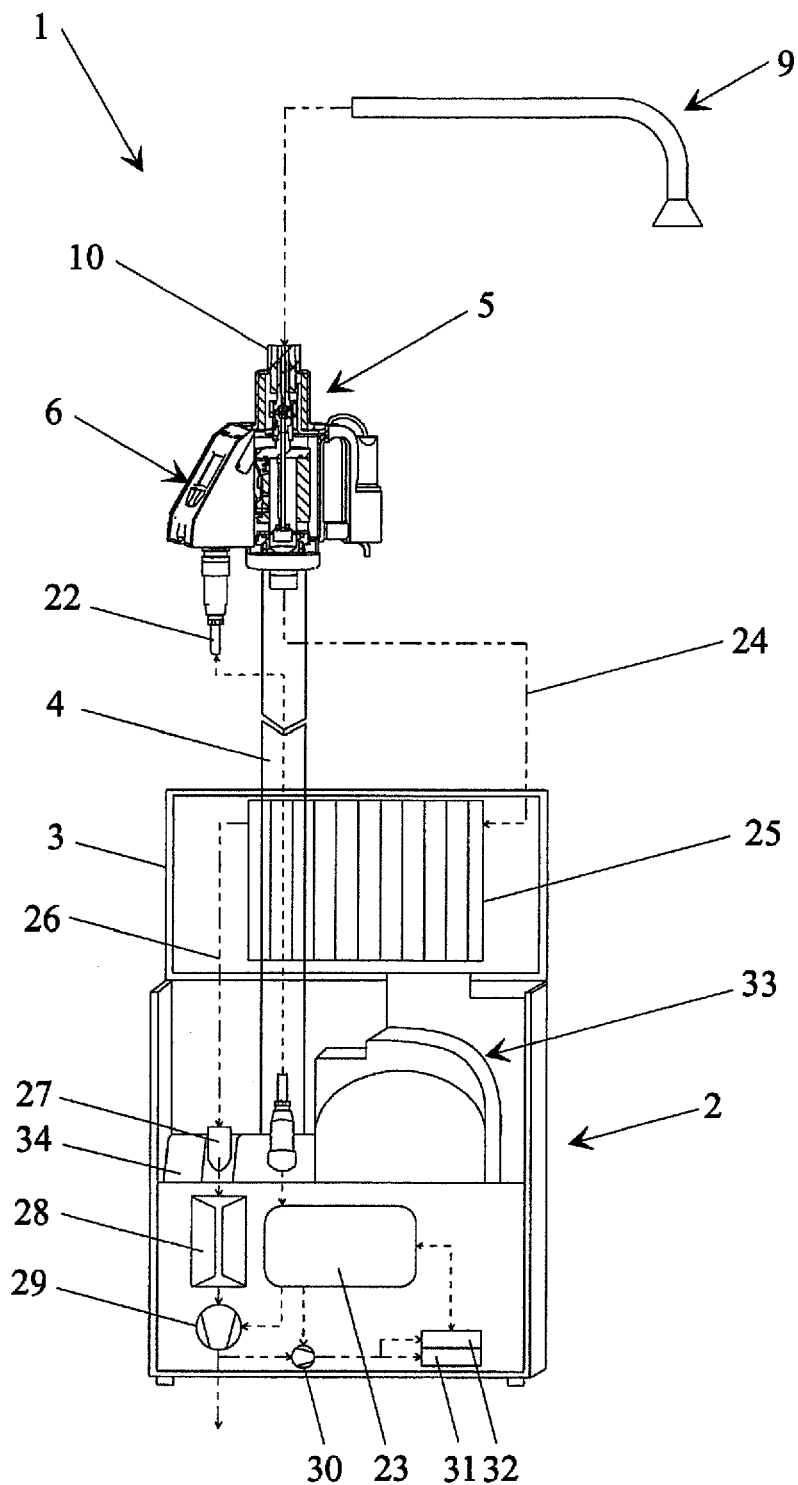
FIG. 1 is a schematic front view of the measuring device overall.

FIG. 1 schematically shows a measuring device 1, according to an embodiment of the invention, which can be accommodated in its entirety in a case 2 for transport or storage. The case 2 has a folding case cover 3 which, as is shown, can be locked in a vertical position. A front flap, not shown in FIG. 1, which extends approximately over half of the height of the case, improves accessibility to the interior of the case.

Figure 2:
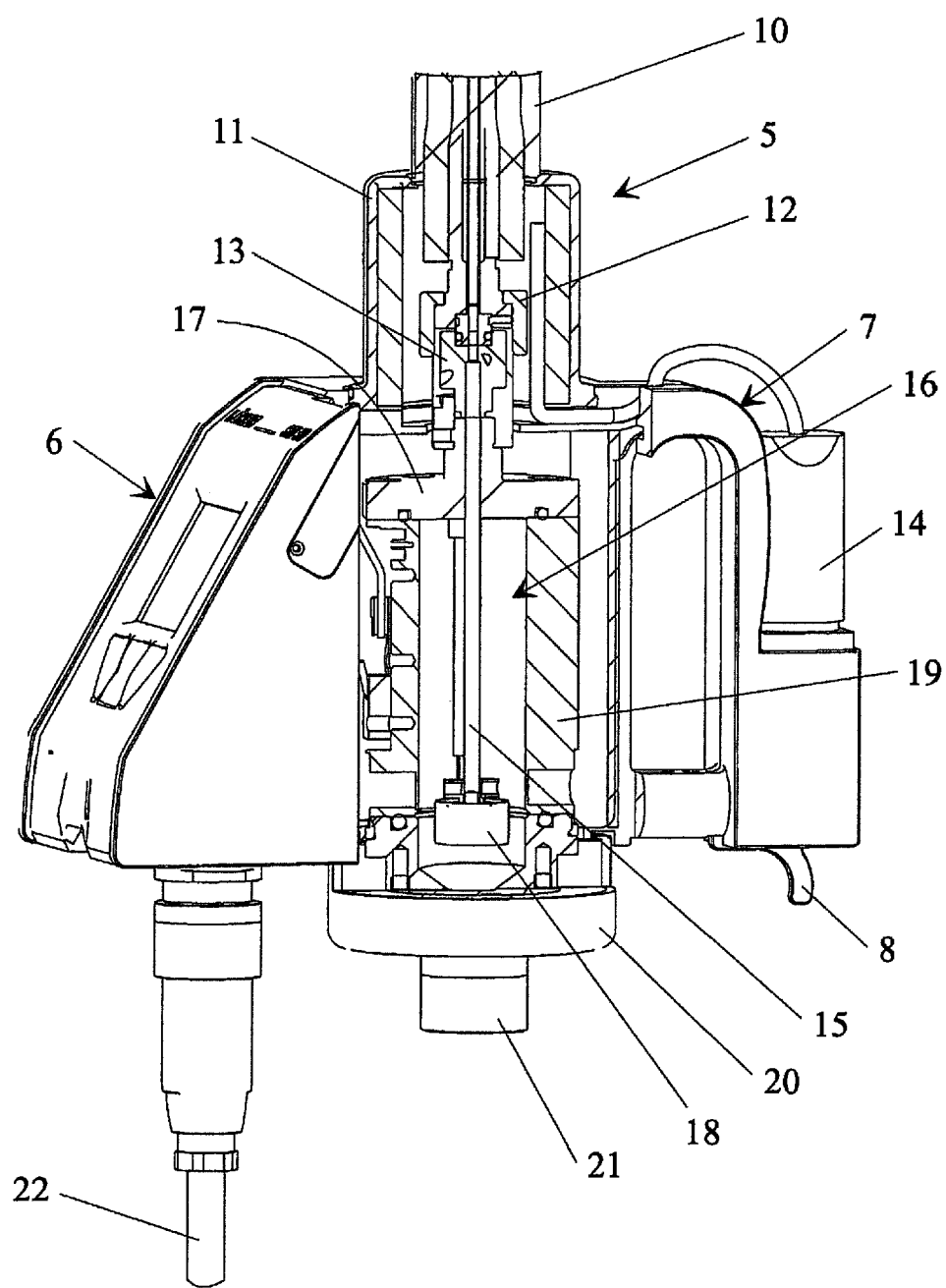
FIG. 2 is an enlarged section through the weighing module with connected display-and-control module.

When the case cover 3 is opened, a weighing module 5 with display-and-control module 6 connected to it, seen most clearly in the enlarged view of FIG. 2, can be pulled out of the interior of the case on a telescoping stand 4 to a convenient working height. A handle 7 is helpful for this purpose, and a lever 8 of a clamping device, for example, by which the weighing module 5 with display-and-control module 6 can be detachably locked to the stand 4, is also arranged at the handle 7.

A heatable suction hose 10 leads from a measuring probe 9 to be introduced into a flue gas flow for measurement to the weighing module 5 and is detachably connected at the weighing module 5. After removing a hose cap 11 and loosening a retainer nut 12, the suction hose can be removed from a hose temperature sensor 13, and the electrical connection to the weighing module 5 can be separated after detaching a plug 14 (see FIG. 2) so that it is possible to clean the suction hose 10 in a simple manner separate from the measuring device 1.

At the other end, the hose temperature sensor 13 is connected to a tube 15 of the weighing device 16.

The tube 15 is fixedly clamped in a cover 17 at one end and at the other, vibratory free end, is closed by an attached filter cartridge 18.

The tube 15 centrally penetrates an evacuable sleeve 19 so as to be closed at the top by cover 17 and on the bottom by a closure cover 20 with a suction hose connection piece 21.

Axial bore holes, not shown in the drawing, which serve to receive heating cartridges, which also make it possible to heat the weighing device 16, are inserted into the wall of the sleeve 19.

An electric connection cable 22 leads from the display-and-control module 6, in which the weighing electronics are also preferably arranged, into the interior of the case and is connected therein to control electronics 23.

A connection hose 24, only shown schematically in FIG. 1, leads from the suction hose connection piece 21 of the weighing module 5 to a flue gas condenser 25. The flue gas condenser 25 is detachably fastened to the vertically lockable case cover 3. A further connection hose 26, shown schematically, is connected to the flue gas condenser 25 on the output side and is connected at the other end via a hose connection 27 with a filter, not shown, to a measuring device 28, shown schematically, for measuring the normal volume flow.

A pump 29, for example, a rotary vane pump controlled by the control electronics 23, generates the differential pressure required for gas throughput, after which the gas that has been sucked out exits into the environment.

The flue gas is supplied to further sensors, e.g., a sensor 31 for $O_2$ and/or a sensor 3 for CO, by a further pump 30, for example, a diaphragm pump controlled by the control electronics 23, and the measurements of the flue gas are evaluated by the control electronics 23 and can be displayed by the display-and-control module 6.

After a measurement has been concluded, the stand 4 with weighing module 5 and display-and-control module 6 is inserted into the case 2 again and the suction hose 10 is set down on a holding device 33. In addition, a cover plate 34 covers the sensor arrangement with sensors 31, 32, measuring device 28, control electronics 23, and pumps 29, 30.

Thus, while there have been shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A measuring device for measuring dust in flue gas of small-scale furnace installations for solid fuels, comprising:
    a measuring probe (9);
    a weighing device (16) having a filter device;
    a heated suction hose (10) connecting the measuring probe (9) to the weighing device (16);
    a weighing module (5) in which the weighing device (16) is arranged, wherein the weighing device (16) is thermally insulated in the weighing module (5);
    a display-and-control module (6) connected to the weighing module (5);
    a case (2); and
    a telescoping stand (4),
    wherein the weighing module (5) is self-contained and configured so as to be removable from the case (2), together with the display-and-control module (6), via the telescoping stand (4).

2. The measuring device according to claim 1, further comprising a heatable sleeve (19) in the weighing module (5), wherein the weighing device (16) is arranged in the heatable sleeve (19).

3. The measuring device according to claim 2, wherein the measuring device is configured to heat the weighing device (16) in a pulsed manner.

4. The measuring device according to claim 2, further comprising a vibratory tube (15) arranged in the heatable sleeve (19), a free end of the vibratory tube (15) being disposed on a gas outlet side of the measuring device and the vibratory tube (15) being terminated by a filter cartridge (18) fitted to the vibratory tube (15).

5. The measuring device according to claim 1, wherein the measuring device is configured to heat the suction hose (10) in a controlled manner.

6. The measuring device according to claim 1, further comprising a hose temperature sensor (13) arranged between the weighing device (16) and the suction hose (10).

7. The measuring device according to claim 1, wherein the weighing module (5) and the display-and-control module (6) are configured so as to be removable from the telescoping stand (4).

8. The measuring device according to claim 1, wherein the case (2) has a folding case cover (3) having a flue gas condenser (25).

9. The measuring device according to claim 1, wherein the case (2) has a front flap.

* * * * *